(12) United States Patent
King et al.

(10) Patent No.: US 6,352,853 B1
(45) Date of Patent: Mar. 5, 2002

(54) MULTI-CHANNEL ELECTRODE ARRAYS

(75) Inventors: Jeffrey S. King, Richmond; Tod A. Flak, San Francisco, both of CA (US)

(73) Assignee: Rosetta Inpharmatics, Inc., Kirkland, WA (US)

( * ) Notice: Subject to any disclaimer, the term of this patent is extended or adjusted under 35 U.S.C. 154(b) by 0 days.

(21) Appl. No.: 09/440,890

(22) Filed: Nov. 16, 1999

Related U.S. Application Data
(60) Provisional application No. 60/111,295, filed on Dec. 7, 1998.

(51) Int. Cl.[7] .................................................. C12M 1/42
(52) U.S. Cl. ................................ 435/285.2; 435/287.2; 435/288.4; 204/403
(58) Field of Search ......................... 435/285.2, 287.2, 435/288.4, 173.6; 204/403, 411, 412

(56) References Cited

U.S. PATENT DOCUMENTS

| | | | |
|---|---|---|---|
| 4,882,281 A | 11/1989 | Hilliard et al. | ............. 435/287 |
| 5,128,257 A | 7/1992 | Baer | ........................ 435/173 |
| 5,137,817 A | 8/1992 | Busta et al. | ................ 435/173 |

FOREIGN PATENT DOCUMENTS

| | | | |
|---|---|---|---|
| EP | 0594282 A2 | 4/1994 | ........... C12M/3/00 |
| EP | 0710718 A1 | 5/1996 | ........... C12M/3/00 |
| WO | WO 95/23211 | 8/1995 | ........... C12N/13/00 |
| WO | WO 98/12310 | 3/1998 | ........... C12N/13/00 |

OTHER PUBLICATIONS

Beckman Coulter, Multimek 96, (1998).

Fiedler, et al., "Diffusional Electrotitration: Generation of pH Gradients over Arrays of Ultramicroelectrodes Detected by Fluorescence", *Anal. Chem.* 67:820–828 (1995).

Neumann, et al., "Calcium–Mediated DNA Adsorption to Yeast Cells and Kinetics of Cell Transformation by Electroporation", *Biophysical Journal* 71:868–877 (1996).

M. Peterfy et al., "Electroporation of COS–7 Cells With Transient Expression Vectors in 96 Well Microplates by Single, 8, and 96 Well Coaxial Electrodes," *Methods In Molecular And Cellular Biology*, 5:353–362, 1995.

*Primary Examiner*—David A. Redding

(57) ABSTRACT

This invention features high-density electrode arrays for use in electroporation. These arrays contain a plurality of electrode pairs where the electrodes in each electrode pair are flat and parallel to each other.

15 Claims, 4 Drawing Sheets

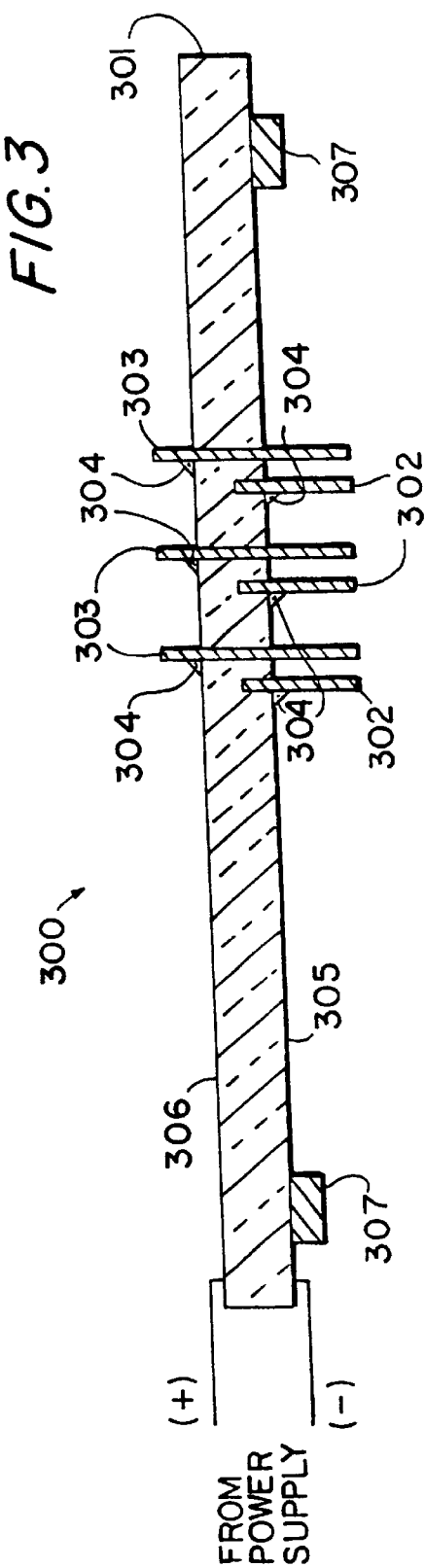
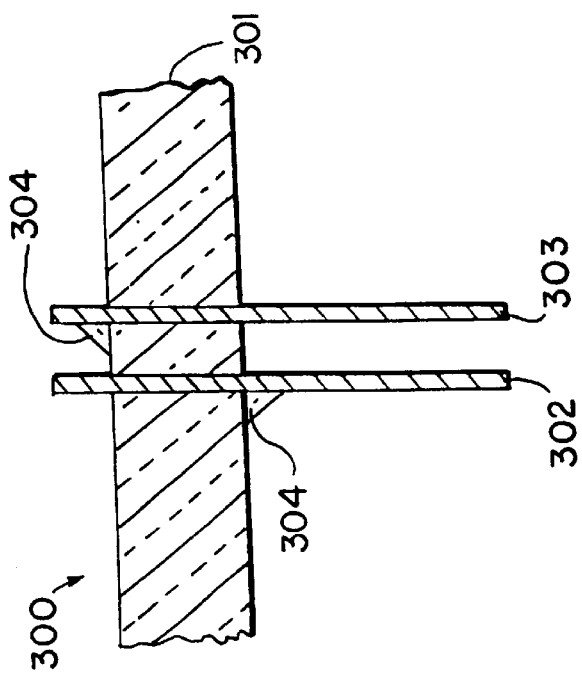
FIG.3
FIG.4

MULTI-CHANNEL ELECTRODE ARRAYS

CROSS REFERENCE TO RELATED APPLICATION

Under 35 U.S.C. §119(e)(1), this application claims the benefit of prior U.S. provisional application No. 60/111,295, filed Dec. 7, 1998.

FIELD OF THE INVENTION

This invention relates to electroporation methods and apparatus for introducing exogenous molecules into lipid vesicles such as cells in vitro.

BACKGROUND OF THE INVENTION

Electroporation is a well established technique for introducting exogenous molecules such as plasmid DNA into cells. It involves the application of a large voltage across a liquid sample containing the cells and the molecules of interest. Typically, electroporation is conducted by positioning a single-channel apparatus that includes a pair of electrodes, i.e., a cathode and an anode, in a sample-containing chamber such as a disposable cuvette. See, e.g., Neumann et al., *Biophysical Journal*, 71, pp. 868–77 (1996).

Multi-channel electrode systems are used for high throughput introduction of exogenous molecules into cells, or to avoid the need for transferring cells from culture containers to electroporation cuvettes. A multi-channel electroporation apparatus includes a plurality of pairs of electrodes positioned in respective ones of a plurality of chambers that hold the exogenous materials and the cells. Currently available multi-channel electroporation devices contain 8 or 96 pairs of coaxial electrodes (Genetronics, Inc., San Diego, Calif.). These devices are used for electroporation in standard 96-well plates, which consist of 8 rows and 12 columns of wells and have a standard size of about 8.5 (W) cm×12.7 cm (L), with a standard center-to-center spacing of 9.0 mm between wells.

SUMMARY OF THE INVENTION

This invention features an electroporation apparatus for introducing exogenous molecules such as nucleic acids, proteins and chemical compounds into vesicles. The apparatus comprises a multi-channel electrode array which contains a plurality of electrode pairs. In each of these electrode pairs, the electrodes are flat and parallel to each other.

Vesicles that can be electroporated in accordance with this invention include, but are not limited to, microscopic or submicroscopic vesicles that contain lipid or fatty acid membrane, e.g., prokaryotic and eukaryotic cells, microsomes and micelles. The vesicles can be unilamellar, bilamellar or multilamellar and range in size, e.g., from 1 nm to 100 $\mu$m.

In one embodiment of the invention, the electrode array contains electrode pairs that are positioned to form a matrix consisting of a plurality of rows and columns of electrode pairs such that each electrode pair can fit into a different well of a multi-well plate.

In one of the preferred embodiments, the number of electrode pairs in the array is a multiple of 96 (e.g., 192, 288, 384, 576, 672, 768 or 1536) and each electrode pair can fit into a different well of a multi-well plate having the same number of wells and the standard size of about 8.5 cm (W)×12.7 cm (L). The reason for this preference is that many currently available microplate instruments were designed specifically for the standard 96-well format and can be readily converted for use with multiples of the 96-well format. Thus, this preference does not in any way limit the scope of the invention.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following drawings, detailed description, and the claims.

BRIEF DESCRIPTION OF THE DRAWINGS

FIG. 3 is a cross-sectional view of an electrode array in accordance with another embodiment of the present invention.

FIG. 4 is a cross-sectional view of the electrode array of FIG. 3 showing an alternative way to attach the electrodes to a nonconductive support.

DETAILED DESCRIPTION OF THE INVENTION

The invention features an electroporation device that contains a plurality of pairs of parallel electrodes. Each of these electrodes may be made of, or coated at least on its inner side with, a conductive material such as gold, copper, tin, platinum, silver, carbon, silicon, an alloy containing one or more of these materials or any other suitable material. Preferably, each electrode is completely flat; however, it may also have a small degree of curvature or bend.

Each pair of electrodes, called a "probe" herein, contains a cathode and an anode and can fit into a well of a multi-well plate. A plurality of such probes is called an electrode array (or matrix) and can be used to simultaneously electroporate samples in two or more rows or columns of wells in a high-density well plate, e.g., a 384-well plate.

The electrode arrays of this invention are relatively easy to manufacture and less subject to the wicking problems that would be encountered in using high-density coaxial multi-channel electrodes. As a result, the new electrode arrays not only increase the number of unique transformations that can be performed simultaneously, but can also significantly reduce the amount of the materials that are transferred out of the electroporation chamber due to the wicking effects of the electrodes. These features allow the manufacture and use of electrode arrays having densities much higher than those allowed by the prior art. For instance, while the currently available multi-channel devices are made for electroporation in standard 96-well plates, this invention provides electrode arrays that can be used to electroporate samples in 384- and 1536-well plates of the same size. The increase in the well density, i.e., decrease in the well size, allows the use of lower amounts of reagents such as cells and DNA for electroporation. To electroporate samples in the wells of a standard 96-well plate, one typically needs about 50–100 μl liquid/well; for a 384-well plate of the same size, as little as 15–25 μl liquid/well is needed.

Figure 1:
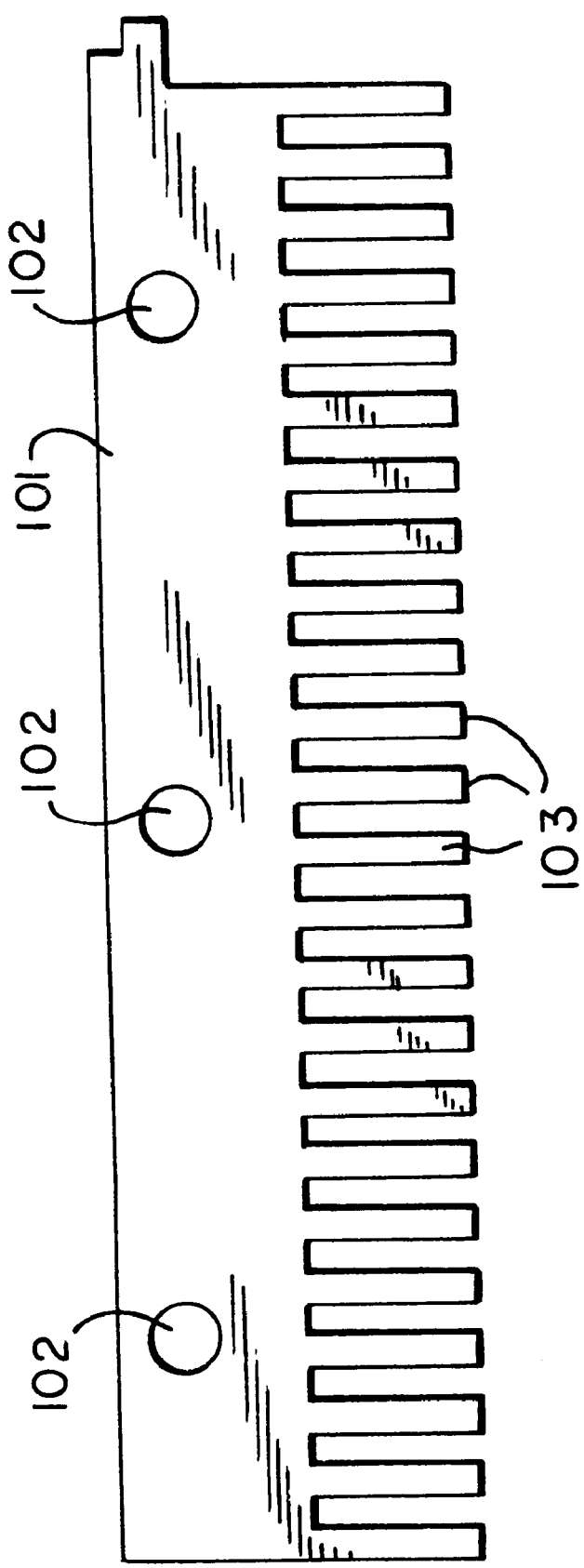
FIG. 1 is an elevational view of a 24-tooth electrode comb that may be used to assemble an electrode array for use in a 384-well (16 rows×24 columns) plate in accordance with one embodiment of the present invention.

To facilitate construction, the electrode array can be made in a "comb" format. By way of example, to make a 384-channel (16×24) electrode array for electroporation in 384-well plates, the cathode or anode for a row of 24 wells may be cut from a single piece of metal or other suitable material to generate a comb with 24 teeth. FIG. 1 shows an elevational view of such a comb 101, with holes 102 on the top part of the comb to facilitate assembly (see FIG. 2 and discussion below) and 24 teeth 103. Thirty-two such electrode-combs, i.e., 16 cathode-combs and 16 anode-combs, are needed for the entire electrode array. The wells of a standard 384-well plate are frustrum-shaped, with the top width being about 3.6 mm, the bottom width being about 2.5 mm, and the height being about 10.03 mm. To be able to fit into such wells while allowing adequate space (about 2 mm) for samples, the electrodes of each probe are preferred to be no more than about 2.25 mm in width and no more than about 0.25 mm in thickness. It may also be desirable to use electrodes made of pliable material, e.g., spring metal brass, so that electrodes that otherwise are too far apart to fit into a well can be slightly bent to fit into the well.

Figure 2:
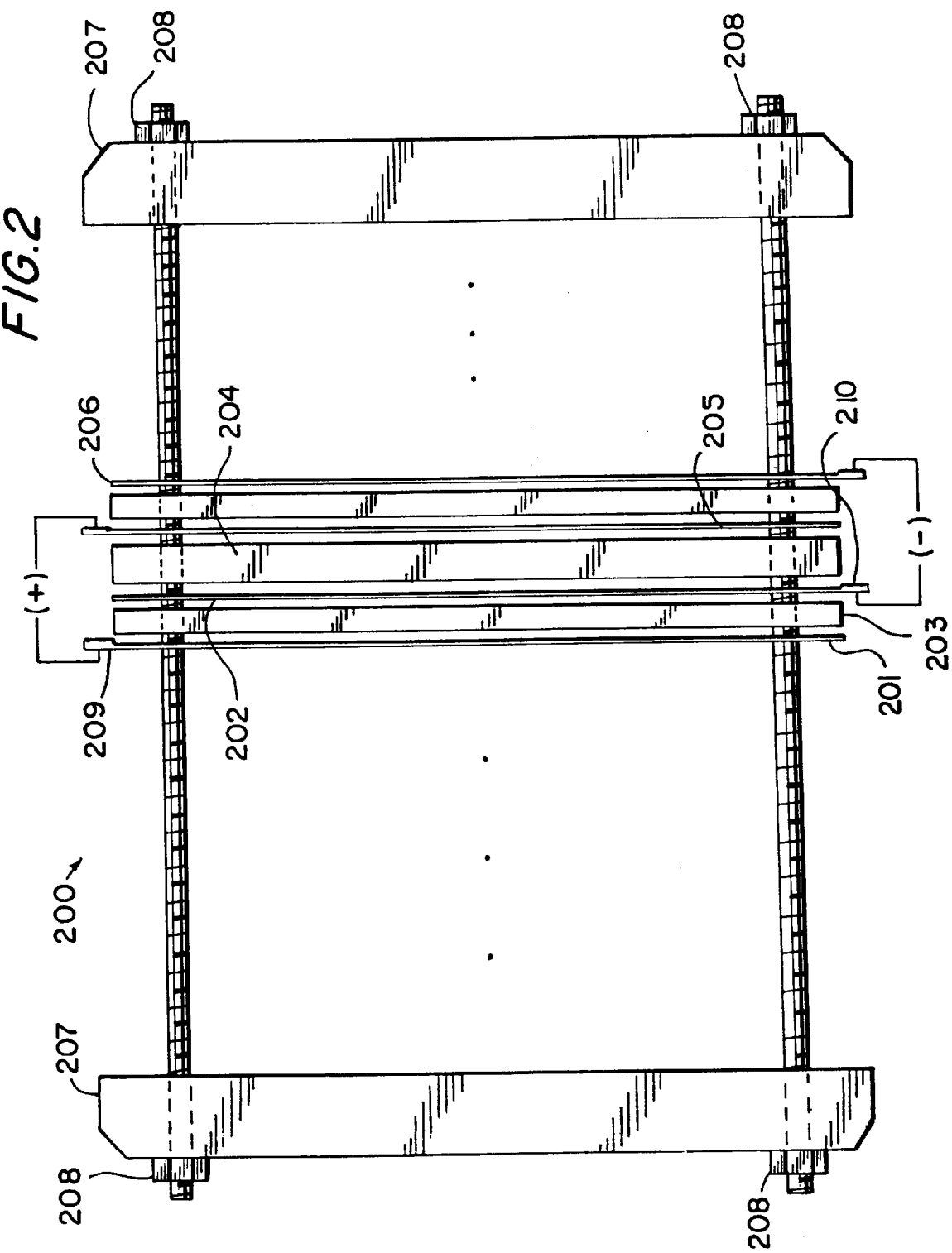
FIG. 2 is a plan view of an electrode array containing a plurality of the electrode combs of FIG. 1 separated by spacers and insulators in accordance with one embodiment of the present invention.

The electrode combs can be sandwiched between pieces of non-conductive material. FIG. 2 shows a plan view of one such electrode array 200. Within array 200, a pair of electrodes 201 and 202 are separated by a spacer 203 such that an even gap exists between the two electrodes. Another pair of electrodes 205 and 206 is separated from the first pair by an insulator 204. End caps 207 and bolts 208 are used to force the electrodes, insulators and spacers into register. Connection tabs 209 and 210, each of which can merely be an extended part of electrode combs 201 and 202, respectively, may be used to connect the combs to a power supply.

Alternatively, the electrode combs can be placed in slots cut into a nonconductive block of plastic such as delrin, TEFLON or any other suitable material. This design can reduce the cumulative errors in the thickness of spacers and insulators generated during the machining process. FIG. 3 shows a cross-sectional view of one such electrode array 300. In array 300, a double-sided circuit board 301 is used as a nonconductive support. Cathodes (or anodes) 302 are fit into notches carved into board 301. Anodes (or cathodes) 303 are pushed through the slits cut into board 301. Copper traces 304 are provided adjacent to cathodes 302 on bottom surface 305 of board 301 and adjacent to anodes 303 on top surface 306 of board 301. Copper traces 304 from the same side of board 301 converge and can be connected to one pole of a power supply. Stoppers 307 are used to prevent the electrode array from being crushed when placed into a well plate.

FIG. 4 shows another way to attach electrodes 302 and 303 to circuit board 301. In FIG. 4, both electrodes are attached to board 301 as shown in FIG. 3, except that electrodes 302, like electrodes 303, also cut through board 301. Of course, other mechanisms, such as the connection tabs 209 and 210 shown in FIG. 2, can be used in lieu of copper traces to connect electrodes to a power source.

Figure 5:
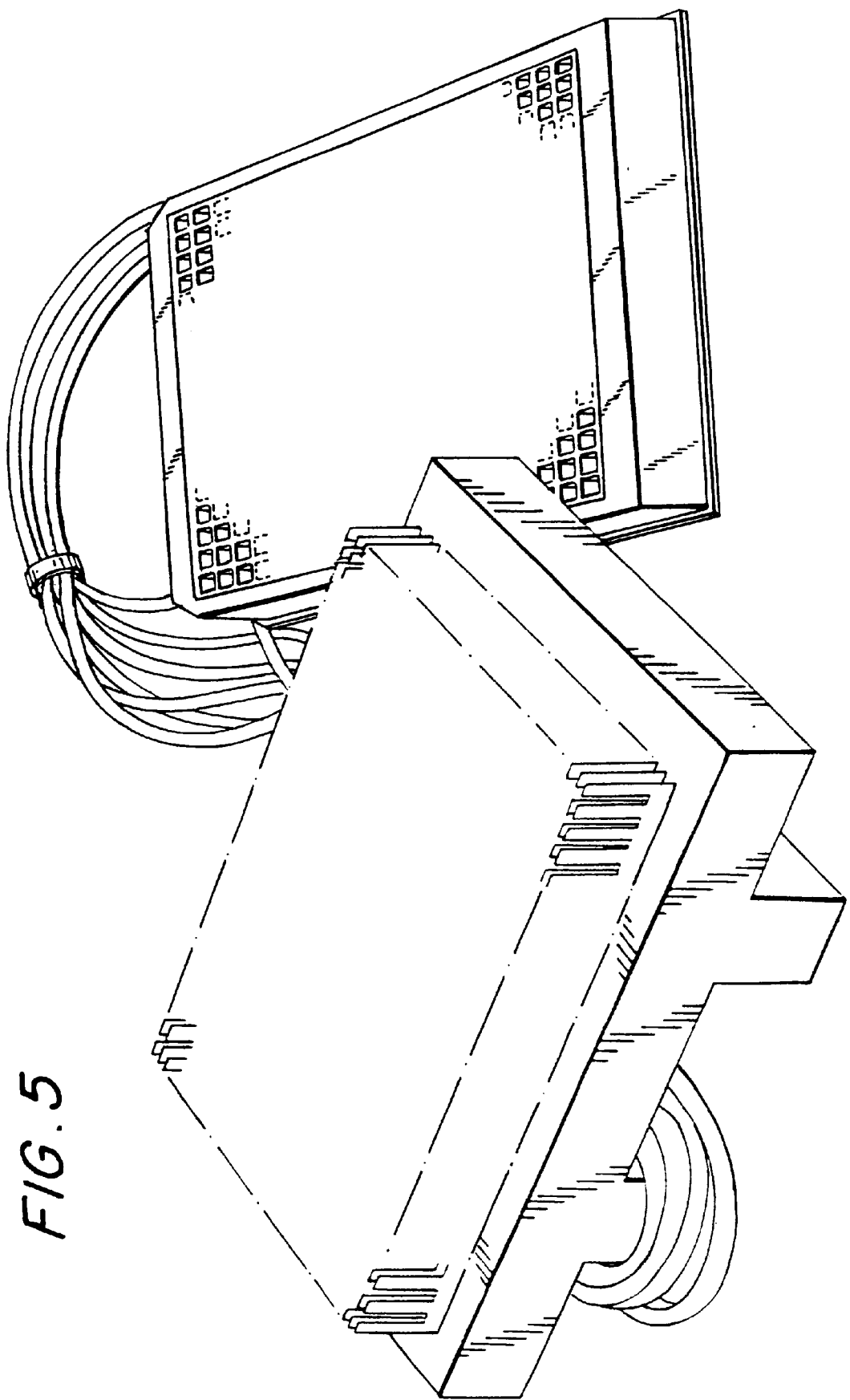
FIG. 5 is a perspective view of an assembled 384-channel electrode array and a 384-well plate in accordance with one embodiment of the present invention.

FIG. 5 shows an assembled 384-well electrode array and a 384-well plate into which the array can fit.

For electroporation, the electrode array may be connected to a capacitance discharge power supply or any other suitable source of power. An exemplary power supply is the BTX Electro Cell Manipulator ECM 600, manufactured by Genetronics (San Diego, Calif.). The ECM 600 can be connected to a 384-channel electrode array through an 8-position tap switch, which is used to discharge power to one eighth of the electrode combs, i.e., 48 pairs of electrodes, at a time. By changing the position of the switch between charge and discharge cycles, all samples in a 384-well plate are subject to electroporation. This switch is used because the ECM 600 has the power capacity to drive only one eighth of the 384-channel electrode array at optimal voltage and capacitance. The switch allows the power supply to deliver more energy per well per pulse and results in more even distribution of the power between wells. With the use of a more powerful power supply, however, such a switch can be eliminated or the number of the switch positions can be reduced.

The following example is meant to illustrate the methods and materials of the present invention. Suitable modifications and adaptations of the described conditions and parameters normally encountered in electroporation which are obvious to those skilled in the art are within the spirit and scope of the present invention.

EXAMPLE 1

Preparation of Competent Cells and Aliquoting DNA

This example describes a protocol for preparing electro-competent yeast cells (i.e., yeast cells that are ready to be electroporated) and for aliquoting DNA into 384 well plates prior to electroporation into yeast cells.

The requisite materials for making electro-competent yeast cells include sterile water, 50 mM β-mercaptoethylamine ("MEA"), 200 mM lithium acetate, electroporation buffer (1 mM calcium acetate, 1 mM Tris (pH 7.2) and 1 M sorbitol), and an autoclaved 96-well block. The necessary stock solutions are 1 M Tris (pH 7.2), 1M filter-sterilized calcium acetate, 2 M filter-sterilized sorbitol and 1M lithium acetate.

Yeast cells are grown in 2.5 L of culture media to a final $OD_{600}$ of 4.0. Meanwhile, the following solutions are prepared: 125 ml of 50 mM β-MEA and 125 ml of 200 mM lithium. After the cell culture reaches the desired density, it is transferred into three 1 L sterile centrifuge bottles and centrifuged at 3000 rpm for 10 minutes. The supernatant is decanted. Sterile water of the same volume as the initial culture volume is added to the cell pellets, which are then resuspended by vigorously shaking the bottles. The cells are centrifuged again at 3000 rpm for 10 minutes. After the supernatant is decanted, 125 ml ($1/20^{th}$ initial cell volume) of 50 mM β-MEA is added to gently resuspend the three cell pellets. Then 125 ml of 200 mM lithium acetate is added and mixed gently with the cells. The cell suspensions are incubated, with the lid loosened, at 30° C. for 30 minutes. After the incubation, the cells are centrifuged at 3000 rpm for 10 minutes. The supernatant is decanted, and 250 ml of sterile water is added to gently resuspend the cells. The cells are again centrifuged at 3000 rpm for 10 minutes, and 250 ml of sterile water is again added to gently resuspend the cells. After the cells are spun down again at 3000 rpm for 10 minutes, they are resuspended in 162.5 ml, i.e., 65 ml for every 1 L initial cell volume, of electroporation buffer.

With the use of a matrix pipette and sterile tips, 1.69 ml of cells is aliquoted into each well of the autoclaved 96-well block. The cells are now ready for electroporation.

DNA is aliquoted into 384 well plates using the MULTI-MEK Automated 96-Channel Pipettor ("MULTIMEK"; Beckman Coulter, Inc. Fullerton, Calif.) or any other suitable pipetting systems. The requisite materials include sterile water, 384-well plates, Perkin-Elmer ("PE") polymerase chain reaction ("PCR") plates, a PE base for holding the plates, sterile pipette tips, adhesive tape for sealing the 384-well plates, a COSTAR plate-sealer, and plates of transforming DNA.

Using the MULTIMEK, a 1:5 dilution of transforming DNA is made in sterile water. The MULTIMEK picks up the pipette tips, transfers 16 μl of water into the empty PE plates, goes into the DNA plates, picks up 4 μl of stock DNA solution, dispenses the DNA into the water in the PE plates, and mixes the water and the DNA. The system is then paused to allow the retrieval of the DNA plates and the placement of two 384-well plates onto the MULTIMEK deck. After being unpaused, the MULTIMEK goes into the PE plates, picks up the diluted DNA, and dispenses 4 μl aliquots into the 384-well plates. The system is then paused again to allow the worker to retrieve the two 384-well plates and put on another two 384-well plates. After being unpaused, the system again dispenses 4 μl of diluted DNA solution into the two new 384-well plates and then goes and unloads the tips. After the MULTIMEK finishes making aliquots for the 384-well plates, the plates are sealed with adhesive tape and stored in a freezer if not to be used immediately. The DNA plates can be sealed with the Costar plate sealer, and stored in a freezer, if desired. The PE plates used to make the DNA dilution can be discarded.

EXAMPLE 2

Electroporation

This example describes a protocol for electroporation using a 384-channel electrode array of this invention.

The following materials are required: 70% and 100% ethanol, a 384-channeled electrode array, two trays that can hold the array during washes, a power source, a sonicator bath, a timer, and an air tube with a filter for drying the ethanol on the electrode after washes. The 70% and 100% ethanol is added to the two trays, respectively. Aliquoted DNA plates, as described above, are thawed at room temperature. Then, the plates are spun at 2500 rpm for 5 minutes.

A MULTIMEK is used to aliquot electro-competent yeast cells into three 384-well plates containing diluted transforming DNA. The 384-channel electrode array is used to electroporate the cells, and then the MULTIMEK is used to plate the electroporated cells onto agar plates containing selective media.

The MULTIMEK aliquots cells from a 96-well block into each of the 384-well DNA plates. One box of tips is used for each cell block. That means four boxes of tips are used for one 384-well plate. Care should be taken to make sure that the cells do not settle out of solution in the 96-well block. If they do, the block should be placed on a a titer-plate shaker to resuspend the cells. Alternatively, the cells can be resuspended manually using a matrix pipette.

The power source settings for electroporation are 1100 V, 50 μF, and 720Ω. Prior to electroporation, the 384-channel electrode array is washed and sterilized by sonication for 10 seconds, soaked in 70% ethanol for 1 minute and in 100% ethanol for 1 minute, and blow-dried with an air tube. Then the electrode array is carefully placed into a 384-well plate containing the DNA and cells. The cells are electroporated in the plate, two rows of wells at a time.

To electroporate, the tap switch located on top of the power source is turned to 1. Once the electrode sits properly in the plate, the RESET button on the power source is pressed, and then the AUTOMATIC CHARGE AND PULSE button is pressed and held down until a click sound is heard and the charging light on the power source stops flashing. Once the power source is recharged, the dial of the switch box is turned to the number of the next two rows of wells and electroporation of those rows is performed as done to the previous rows. This procedure is repeated until all sixteen rows of the 384-well plate are electroporated.

The MULTIMEK is then used to take out and plate 6 μl of the electroporated cells from each well of the 384-well plate onto casamino acid agar plates in a 96-well format. When plating, care should be taken to make sure that cells remain in their unique positions and that the droplets do not run into each other and that all 96 spots on the agar plate have a patch of liquid containing the cells. When the plating is completed, each patch of liquid on the agar plate should be dry. Then the plate is flipped upside down and incubated at 30° C. for 2–3 days. After 2–3 days of incubation, transformed cells will grow into visible colonies.

EXAMPLE 3

Experimental Data

This example describes the experimental data obtained in transforming yeast cells with reporter plasmids using the above protocols.

A 384-channel electrode array of this invention was used. The plasmid DNA was added to four 96-well blocks, and the material in each well of the blocks was then roboticly transferred to a 384-well plate. A yeast strain, either "wild type" or mutant, was grown and made electro-competent. The electro-competent cells were then roboticly transferred into a 384-well plate containing plasmid DNA. An electrical pulse was applied to each well in the 384-well plate using the electrode array. The cells were then plated onto solid media at a density of 96 electroporated samples per plate.

Approximately one hundred yeast strains were each transformed with more than 6,000 unique plasmids. In a typical transformation, greater than 97% of patches had more than 10 colonies per patch. Less than 2% had no transformants. A likely cause of no transformants was liquid handling errors—either the DNA was not evenly dispensed or heterogeneity in sample preparations of cells and DNA resulted in uneven electroporation. Approximately $200 \times 10^{-6}$ μg of DNA per plasmid, were used per transformation, and a typical patch had approximately 100colonies, yielding a transformation efficiency of $0.5 \times 10^6$ transformants/μg.

Other Embodiments

It is to be understood that while the invention has been described in conjunction with the detailed description thereof, the foregoing description is intended to illustrate and not to limit the scope of the invention, which is defined by the scope of the appended claims. Other aspects, advantages, and modifications are within the scope of the following claims.

What is claimed is:

1. An electroporation apparatus for introducing an exogenous molecule into a vesicle, the apparatus comprising a plurality of electrode pairs, wherein the electrodes in each of the electrode pairs are flat and parallel to each other and wherein the electrode pairs are positioned to form a matrix consisting of a plurality of electrode pairs and a plurality of columns of electrode pairs.

2. The apparatus of claim 1 wherein each row of the electrode pairs comprises two comb-shaped conductive pieces and each of the electrode pairs in the row consists of two aligned teeth of the two comb-shaped conductive pieces.

3. The apparatus of claim 1 wherein the number of the electrode pairs is a multiple of 96 and each of the electrode pairs fits into a different well of a multi-well plate that has a standard size and said number of wells.

4. The apparatus of claim 3 wherein the number of the electrode pairs is selected from the group consisting of 192, 288, 384, 576, 672, 768 and 1536.

5. The apparatus of claim 3 wherein the matrix consists of 16 rows and 24 columns and the electrode pairs are positioned such that each electrode pair fits into a different well of a 384-well plate.

6. The apparatus of claim 3 wherein the linear matrix consists of 32 rows and 48 columns and the electrode pairs are positioned such that each electrode pair fits into a different well of a 1536-well plate.

7. The apparatus of claim 1 wherein the vesicle comprises a lipid membrane.

8. The apparatus of claim 7 wherein the vesicle is a cell.

9. The apparatus of claim 7 wherein the vesicle is a microsome.

10. The apparatus of claim 8 wherein the electrode pairs are positioned to form a matrix consisting of 16 rows and 24 columns and each of the electrode pairs fits into a different well of a 384-well plate.

11. The apparatus of claim 1 wherein the exogenous molecule is a nucleic acid.

12. The apparatus of claim 11 wherein the vesicle is a cell.

13. The apparatus of claim 1 wherein the exogenous molecule is a protein.

14. The apparatus of claim 13 wherein the vesicle is a cell.

15. The apparatus of claim 1 wherein the electrode pairs comprise gold.

* * * * *